(12) United States Patent
Cardinali

(10) Patent No.: US 8,945,031 B2
(45) Date of Patent: Feb. 3, 2015

(54) PADDING ASSEMBLY FOR AN ORTHOPEDIC BRACE SELECTIVELY CONFIGURABLE FOR CREATING A WOUND BRIDGE

(75) Inventor: Mathew Cardinali, San Diego, CA (US)

(73) Assignee: Breg, Inc., Carlsbad, CA (US)

( * ) Notice: Subject to any disclaimer, the term of this patent is extended or adjusted under 35 U.S.C. 154(b) by 160 days.

(21) Appl. No.: 13/594,373

(22) Filed: Aug. 24, 2012

(65) Prior Publication Data

US 2014/0058303 A1 Feb. 27, 2014

(51) Int. Cl.
*A61F 5/00* (2006.01)
*A61F 5/37* (2006.01)

(52) U.S. Cl.
USPC .............................................. 602/5; 128/882

(58) Field of Classification Search
USPC .............. 128/881–882, 889, 891, 894, 106.1, 128/112.1; 602/5, 23, 26; 428/137–138
See application file for complete search history.

(56) References Cited

U.S. PATENT DOCUMENTS

| | | |
|---|---|---|
| 1,473,392 A | 11/1923 | Buckley |
| 5,782,780 A | 7/1998 | Mason |
| 5,807,294 A | 9/1998 | Cawley |
| 6,892,734 B1 * | 5/2005 | Schleicher et al. ........... 128/889 |
| 7,485,103 B2 | 2/2009 | Mason |
| 7,713,225 B2 | 5/2010 | Ingimundarson |
| 2009/0049712 A1 | 2/2009 | Steszyn |
| 2012/0016283 A1 | 1/2012 | Hollister |

FOREIGN PATENT DOCUMENTS

WO 2010071170 A1 6/2010

* cited by examiner

*Primary Examiner* — Patricia Bianco
*Assistant Examiner* — Ophelia A Hawthorne
(74) *Attorney, Agent, or Firm* — Rodney F. Brown

(57) ABSTRACT

A padding assembly has two bridging segments and a base pad. The base pad is attachable to an orthopedic brace while the first bridging segment is releasably attached to a mounting substrate on the base pad and the other bridging segment is releasably attached to the same mounting substrate or to another mounting substrate on the brace. The attached bridging segments are spaced apart from one another and the resulting space between them, termed a wound bridge area, has a thickness substantially less than that of the padding assembly at the first bridging segment or that of the other bridging segment.

28 Claims, 8 Drawing Sheets

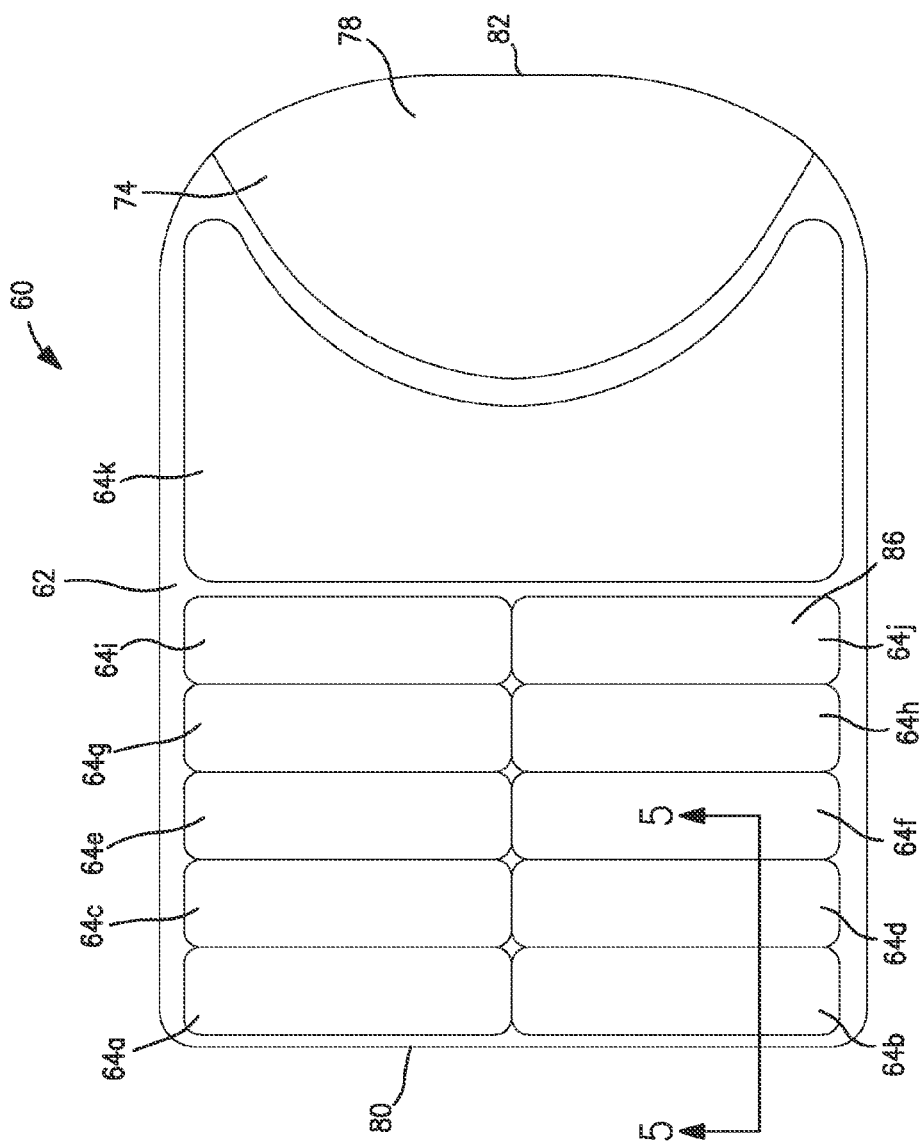

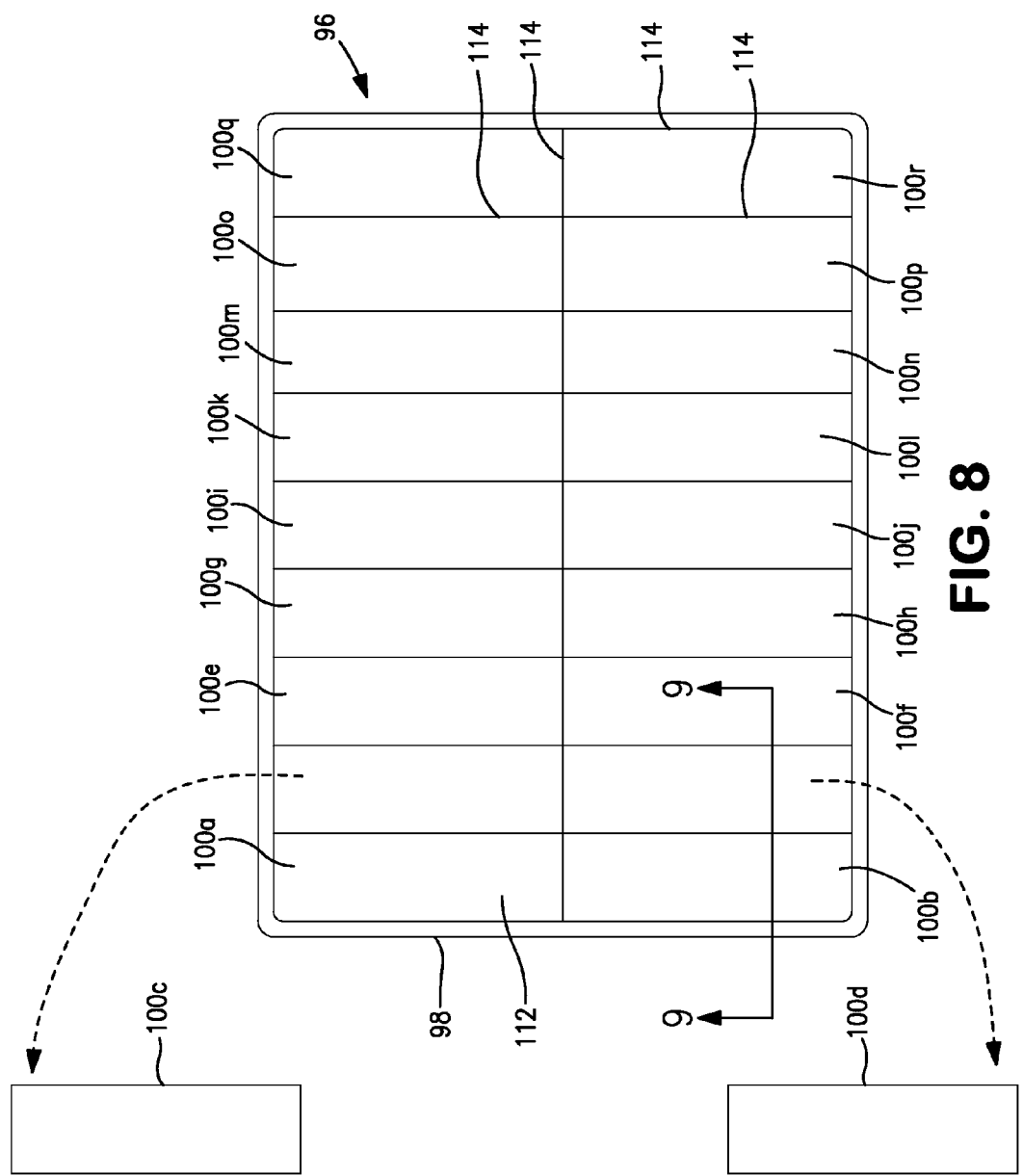

PADDING ASSEMBLY FOR AN ORTHOPEDIC BRACE SELECTIVELY CONFIGURABLE FOR CREATING A WOUND BRIDGE

BACKGROUND OF THE INVENTION

The present invention relates generally to orthopedic braces, and more particularly to a padding assembly which is positioned between an associated orthopedic brace and the body of a wearer.

Orthopedic braces embody a broad range of structures, each having the common purpose of supporting and/or stabilizing a region of the body such as a skeletal joint when the brace is appropriately positioned on the body of a wearer. The orthopedic brace generally serves either a preventative role or a remedial role. For example, in a preventative role the brace may provide added support and stability to a healthy skeletal joint, thereby reducing the risk of injury when the joint is subjected to undue stress. In a remedial role, the brace may support and stabilize a skeletal joint which has been weakened by injury or other infirmity, thereby reinforcing the joint and reducing the risk of further injury while the joint is rehabilitated.

Conventional orthopedic braces typically have a support member positioned in abutment with a region of the body which is intended to benefit from the added support or stability provided by the brace. In cases where the orthopedic brace is intended to support and/or stabilize a skeletal joint, the brace typically has multiple support members which are positioned on the opposite sides of the joint. The support members may be dynamically interconnected by a hinge which is positioned at the skeletal joint to mimic the motion of the joint. For example, a conventional knee brace commonly includes a rigid frame having an upper support member positioned adjacent to the upper leg of the wearer and a lower support member positioned adjacent to the lower leg of the wearer. A rotational hinge is positioned adjacent to the knee joint of the wearer which dynamically interconnects the upper and lower support members enabling controlled pivotal movement of the knee joint when the wearer engages in activity or rehabilitative therapy.

Orthopedic braces are typically secured to the body of the wearer at a desired mounting position by securing means such as straps which engage both the body and the support members of the brace. Orthopedic braces also typically have one or more compressible pads which cushion the body of the wearer from the support members of the brace. The pads commonly attach to and cover the inner surface of the support members, thereby providing the orthopedic brace with a soft comfortable contact surface against the skin and insulating the skin from direct contact with the support members. The pads also enhance the functional performance of the orthopedic brace by providing a close fit of the brace to the body of the wearer and resisting migration of the brace from the desired mounting position on the body during use.

Although brace pads are generally effective for the above-described cushioning, fitting and anti-migration functions, one drawback is the occasional need to position the brace pads and their overlying support members atop wound sites in order to effect a proper positioning of the brace on the body. This problem is particularly acute when the orthopedic brace is used for post-operative applications where it is common for a brace pad to overlay a surgical wound. Even if the wound is protected by a dressing, contact between the pad and the dressing and/or underlying wound undesirably inhibits wound healing because pad coverage blocks air circulation to the wound and pad compression chafes or otherwise irritates the wound.

The present invention recognizes the importance and need for an orthopedic brace which does not inhibit the healing of a wound when the brace is mounted atop the wound site. Accordingly, it is an object of the present invention to provide an orthopedic brace which substantially avoids contact between the brace and an underlying wound when the brace is mounted on the body of a wearer. More particularly, it is an object of the present invention to provide an orthopedic brace with a padding assembly positioned between the brace and the body of the wearer which has a wound bridge formed thereon, wherein the padding assembly contacts the skin of the wearer away from the wound, but the wound bridge maintains a sufficient clearance between the wound and padding assembly so that the padding assembly substantially avoids contact with the wound, thereby advantageously exposing the wound to the surrounding air and substantially preventing compression of the padding assembly against the wound. It is another object of the present invention to provide an orthopedic brace with a padding assembly which effectively performs the wound-bridging function without diminishing the cushioning, fitting and anti-migration functions of the padding assembly. It is yet another object of the present invention to provide an orthopedic brace with a padding assembly, wherein the location of the wound bridge on the padding assembly is selectively adjustable in correspondence with the relative positions of the wound and the orthopedic brace when mounted on the body of a wearer. These objects and others are accomplished in accordance with the invention described hereafter.

SUMMARY OF THE INVENTION

One characterization of the present invention is a padding assembly having a first surface and a second surface which are preferably on substantially opposite sides of the padding assembly from one another. The first surface of the padding assembly is attachable to an associated orthopedic brace and, in particular, is preferably attachable to a substantially rigid support member of the associated orthopedic brace. The padding assembly comprises a mounting substrate, a first bridging segment and a second bridging segment. The first and second bridging segments are releasably attached to the mounting substrate and are included in a first array which is selectively reconfigurable to a second array. The first array is reconfigured to the second array by detaching the second bridging segment from the mounting substrate to define a first wound bridge area on the second surface of the padding assembly where the second bridging segment is detached. Detachment of the second bridging segment also defines a first raised area on the second surface of the padding assembly where the first bridging segment remains attached. The detached second bridging segment may be selectively attachable to an alternate mounting substrate on the associated orthopedic brace which is preferably a securing strap of the associated orthopedic brace. Alternatively the padding assembly may further comprise an additional third bridging segment which is selectively attachable to the alternate mounting substrate. In any case, the thickness of the padding assembly at the first raised area is substantially greater than the thickness of the padding assembly at the first wound bridge area. Correspondingly, the height of the second surface of the padding assembly at the first raised area is also preferably substantially greater than the height of the second surface of the padding assembly at the first wound bridge area.

In accordance an embodiment of the present invention, the second array is also selectively reconfigurable to a third array by reattaching the detached second bridging segment to the mounting substrate at the first wound bridge area which converts the first wound bridge area to a second raised area. The first bridging segment is also detached from the mounting substrate at the first raised area which converts the first raised area to a second wound bridge area. The thickness of the padding assembly at the second raised area is substantially greater than the thickness of the padding assembly at the second wound bridge area. Correspondingly, the height of the second surface of the padding assembly at the second raised area is also preferably substantially greater than the height of the second surface of the padding assembly at the second wound bridge area.

The padding assembly of the present embodiment may also comprise a third bridging segment which is included in the first array and is releasably attached to the mounting substrate. The second bridging segment is positioned between the first and third bridging segments. As such, the second array defines a second raised area on the second surface of the padding assembly where the third bridging segment is attached. The thickness of the padding assembly at the second raised area is substantially greater than the thickness of the padding assembly at the first wound bridge area. Correspondingly, the height of the second surface of the padding assembly at the second raised area is also preferably substantially greater than the height of the second surface of the padding assembly at the first wound bridge area.

An alternate characterization of the present invention is a padding assembly comprising a base pad and first and second bridging segments. The base pad has a first surface and a second surface. The first surface is attachable to an associated orthopedic brace. The first bridging segment is releasably attached to a first location on a first mounting substrate on the second surface of the base pad. The second bridging segment is releasably attached to a second location. The second location may be on the first mounting substrate or may alternatively be on a second mounting substrate which is on a securing strap or a support element of the associated orthopedic brace. A first wound bridge area is positioned on the first mounting substrate between the first bridging segment and the second bridging segment. The thickness of the padding assembly where the first bridging segment is attached to the first mounting substrate is substantially greater than the thickness of the padding assembly at the first wound bridge area and the thickness of the second bridging segment is substantially greater than the thickness of the padding assembly at the first wound bridge area.

In accordance with an embodiment of the present invention, the first and second locations are on the first mounting substrate and the first and second bridging assemblies and the first wound bridge area are included in a first array. The padding assembly further comprises an additional third bridging segment releasably attached to the first mounting substrate and included in the first array. The first bridging segment is positioned between the third bridging segment and the second bridging segment. The thickness of the padding assembly where the third bridging segment is attached to the first mounting substrate is substantially greater than the thickness of the padding assembly at the first wound bridge area.

The first array is also preferably selectively reconfigurable to a second array by detaching the first bridging segment from the mounting substrate and attaching the detached first bridging segment or an additional fourth bridging segment of the padding assembly to the mounting substrate at the first wound bridge area. This converts the first wound bridge area to a raised area and defines a second wound bridge area where the first bridging segment is detached from the mounting substrate. The thickness of the padding assembly at the raised area is substantially greater than the thickness of the padding assembly at the second wound bridge area and the thickness of the padding assembly where the second bridging segment is attached to the first mounting substrate is substantially greater than the thickness of the padding assembly at the second wound bridge area.

Another characterization of the present invention includes the above-recited padding assembly comprising the base pad and the first and second bridging segments. Both of the first and second bridging segments are releasably attached to the first mounting substrate on the second surface of the base pad and the first wound bridge area is positioned between them. The first and second bridging segments and the first wound bridge are included in a first array. The first array is selectively reconfigurable to a second array by detaching the first bridging segment from the mounting substrate and attaching the detached first bridging segment or an additional third bridging segment of the padding assembly to the mounting substrate at the first wound bridge area, which converts the first wound bridge area to a raised area and defines a second wound bridge area where the first bridging segment is detached from the mounting substrate. The thickness of the padding assembly at the raised area is substantially greater than the thickness of the padding assembly at the second wound bridge area and the thickness of the padding assembly where the second bridging segment is attached to the first mounting substrate is substantially greater than the thickness of the padding assembly at the second wound bridge area.

Another characterization of the present invention also includes the above-recited padding assembly comprising the base pad and the first and second bridging segments. The first bridging segment is releasably attached to the first mounting substrate on the second surface of the base pad and the second bridging segment is releasably attached to a second mounting substrate. The second mounting substrate may be on a securing strap or a support element of the associated orthopedic brace. The first wound bridge area is positioned on the first mounting substrate between the first bridging segment and the second bridging segment. The first and second bridging segments and the first wound bridge are included in a first array. The first array is selectively reconfigurable to a second array by detaching the second bridging segment from the second mounting substrate and attaching the second bridging segment or an additional third bridging segment of the padding assembly to the first mounting substrate at the first wound bridge area, which converts the first wound bridge area to a raised area and defines a second wound bridge area where the first bridging segment is detached from the mounting substrate. The thickness of the padding assembly at the raised area is substantially greater than the thickness of the padding assembly at the second wound bridge area and the thickness of the padding assembly where the second bridging segment is attached to the first mounting substrate is substantially greater than the thickness of the padding assembly at the second wound bridge area.

The invention will be further understood from the accompanying drawings and description.

BRIEF DESCRIPTION OF THE DRAWINGS

FIG. 4 is a plan view of a padding assembly of the present invention.

FIG. 8 is a plan view of an alternate embodiment of a padding assembly of the present invention being configured to provide a wound bridge over a surface wound when the padding assembly is attached to an associated orthopedic brace mounted on a wearer.

Figure 1:
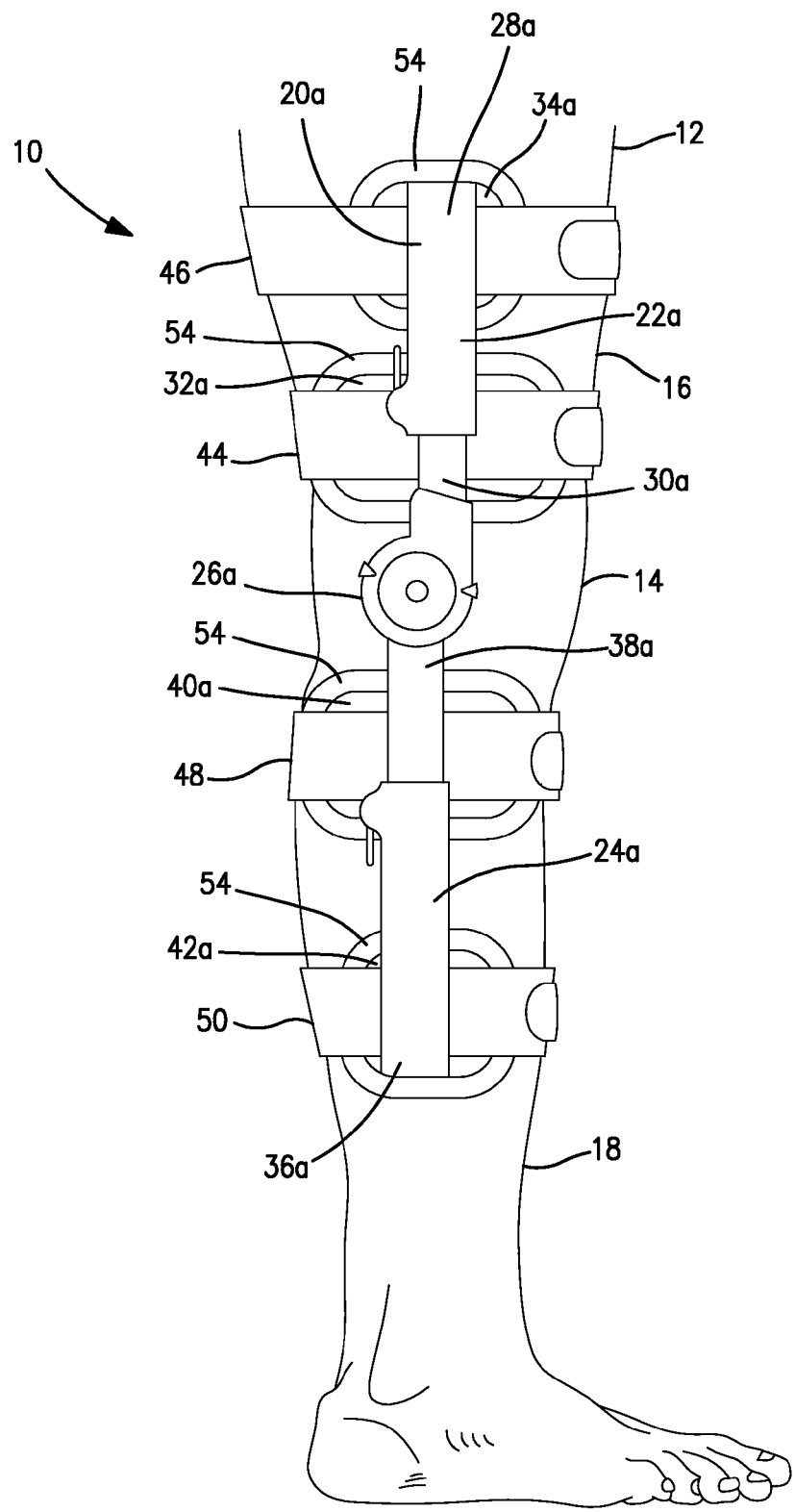
FIG. 1 is a lateral elevational view of a post-op knee brace mounted on the fully-extended leg of a wearer. The post-op knee brace has utility with the associated padding assembly of the present invention.

The above-listed drawing figures illustrate one or more embodiments of the present invention by way of example and not by way of limitation. Common reference characters are used among the different drawing figures to indicate the same or similar structural elements. However, the terms "an embodiment of the invention", "one embodiment of the invention", "an alternate embodiment of the invention", "a preferred embodiment of the invention", or similar such terminology appearing below do not necessarily indicate the same embodiment of the invention when there are multiple occurrences of the same term.

DESCRIPTION OF PREFERRED EMBODIMENTS

The present invention is a padding assembly for an associated orthopedic brace. An associated orthopedic brace which has utility with the padding assembly of the present invention is generally characterized as being configured for mounting on the body of a person at a specific position where supplemental support is desired. As such, the orthopedic brace includes one or more support elements which abut the body and provide supplemental support to the body at the desired mounting position. A typical mounting position of the orthopedic brace is across a joint of the wearer such as a knee, ankle, hip, elbow, wrist or shoulder. The orthopedic brace may optionally be secured in its desired mounting position by one or more securing straps which are connected to the one or more support elements.

The one or more support elements of the associated orthopedic brace may be substantially hard rigid structures which are constructed from substantially rigid or semi-rigid materials. An example of an associated orthopedic brace having multiple rigid support elements is a knee brace having a hinged frame which is mounted on the leg abutting the knee joint. The frame is constructed from one or more rotational hinges and a plurality of substantially rigid support elements which are dynamically joined to one another at the knee joint by the rotational hinges.

Alternatively, the one or more support elements of the associated orthopedic brace may be substantially soft pliant, i.e., flexible, structures constructed from substantially non-rigid or soft pliant materials. An example of a brace having a soft support element is a knee brace constructed in a continuous tubular configuration from a pliant elastic material which functions as a soft support element. The knee brace slides over and encloses the knee joint in the manner of a sleeve.

In yet another alternative, the associated orthopedic brace may have multiple support elements which are a combination of both rigid and soft support elements. An example of a brace having both rigid and soft support elements is a knee brace having a sheet of soft pliant material which wraps around the leg at the knee joint and releasably fastens to itself, thereby enclosing the knee joint and functioning as a soft support element. The sheet is provided with one or more longitudinal pockets and a rigid support element is inserted into and retained by each longitudinal pocket.

It is apparent from the above that the term "rigid" as used herein generally encompasses structures which are deemed either rigid or semi-rigid, but not non-rigid or soft, as these terms are commonly understood. Exemplary rigid or semi-rigid materials of construction include metals, plastics, fiberglass, composites, combinations thereof, or other like, relatively stiff materials. Exemplary non-rigid or soft materials of construction include synthetic or natural cloths, fabrics, foams, laminates, combinations thereof, or other like, relatively pliant materials. In sum, a support element is characterized as "rigid" to the extent it is substantially less flexible, i.e., substantially stiffer, than a support element which is characterized as "soft."

In any case, the associated orthopedic brace, including its support element(s) and optional securing strap(s), if present, has multiple surfaces. Each surface of the associated orthopedic brace is characterized as having either an inner or an outer orientation. The inner surfaces of the associated orthopedic brace are configured to face toward the body of the wearer and away from the surrounding external environment when the brace is mounted on the body. Conversely, the outer surfaces of the associated orthopedic brace are configured to face toward the surrounding external environment and away from the body of the wearer the brace is mounted on the body.

The padding assembly of the present invention is configured to be positioned between the associated orthopedic brace and the body of the wearer when the brace is mounted on the body. More particularly, the padding assembly is configured to be positioned between the body of the wearer and a support element of the associated orthopedic brace and/or an optional securing strap, if present, when the brace is mounted on the body. The padding assembly, like the associated orthopedic brace, has multiple surfaces which may be characterized as having either an inner or an outer orientation. The inner surfaces of the padding assembly are configured to face away from the inner surfaces of the associated orthopedic brace and toward the body of the wearer, thereby engaging the skin of the wearer when the brace is mounted on the body. Conversely, the outer surfaces of the padding assembly are configured to face away from the body of the wearer and toward the inner surfaces of the associated orthopedic brace, thereby engaging the inner surfaces of the brace when the brace is mounted on the body.

The padding assembly of the present invention desirably and advantageously performs inter alia a shielding/cushioning function when the associated orthopedic brace is mounted on the body with the padding assembly positioned between the associated orthopedic brace and the body of the wearer as described above. Specifically, the padding assembly performs the shielding/cushioning function by shielding the body of the wearer from direct contact with the associated orthopedic brace when the brace is mounted on the body. Accordingly, the padding assembly cushions body of the wearer from the support elements of the associated orthopedic brace and the optional securing straps, if present. This function is particularly desirable when the support element is substantially rigid.

Exemplary padding assemblies of the present invention and associated orthopedic braces are described below with reference to the drawings for purposes of disclosing preferred embodiments of the invention. However, it understood that the present invention is not limited to these specific preferred embodiments, but is generally applicable to any padding assembly constructed in accordance with the teaching herein and to any orthopedic brace having one or more rigid and/or soft support elements which can be fitted with a padding assembly.

In accordance with one preferred embodiment, the padding assembly of the present invention can have utility with a specific orthopedic knee brace known in the art as a post-operative (post-op) knee brace which is shown in FIG. 1 and generally designated 10 therein. The general features of the post-op knee brace 10, but not the specific features of the padding assembly of the present invention, are conventional and are disclosed in commonly-owned U.S. Patent Application Publication Nos. 2006/0155229 A1 to Ceriani et al. and 2006/0155232 A1 to Ceriani, both of which are incorporated herein by reference. Post-op knee braces of this same type are available from Breg, Inc., Carlsbad, Calif., U.S.A., under the registered trademark T-SCOPE.

The post-op knee brace 10, as shown in FIG. 1, is operatively mounted on the leg 12 of a patient wearer requiring or desiring added external support and/or stabilization of the knee joint 14 following surgery. When worn on the leg 12, the post-op knee brace 10 specifically engages the knee joint 14, the upper leg 16 above the knee joint 14 and the lower leg 18 below the knee joint 14. For purposes of illustration, the post-op knee brace 10 is configured for securing to the right leg 12 of the patient wearer. However, it is readily apparent to the skilled artisan that the post-op knee brace 10 can be adapted for securing to the opposite leg of the patient wearer.

There are a number of relative terms defined below which are used in the following description to distinguish various elements of the post-op knee brace 10 from one another, but which are not to be construed as limiting the scope of the present invention. The relative terms "medial" and "lateral" describe the relative proximity of certain elements to the central longitudinal axis of the body of the wearer when the post-op knee brace 10 is secured to a leg of the wearer. A "medial" element is closer to the central longitudinal axis of the body, while a "lateral" element is further from the central longitudinal axis of the body. The terms "upper" and "lower" describe the position of certain elements as being either above or below the rotational hinges of the post-op knee brace 10 and correspondingly either above or below the knee joint. An "upper" element is above the rotational hinges and knee joint and proximal to the upper leg 16, while a "lower" element is below the rotational hinges and knee joint and proximal to the lower leg 18.

Figure 2:
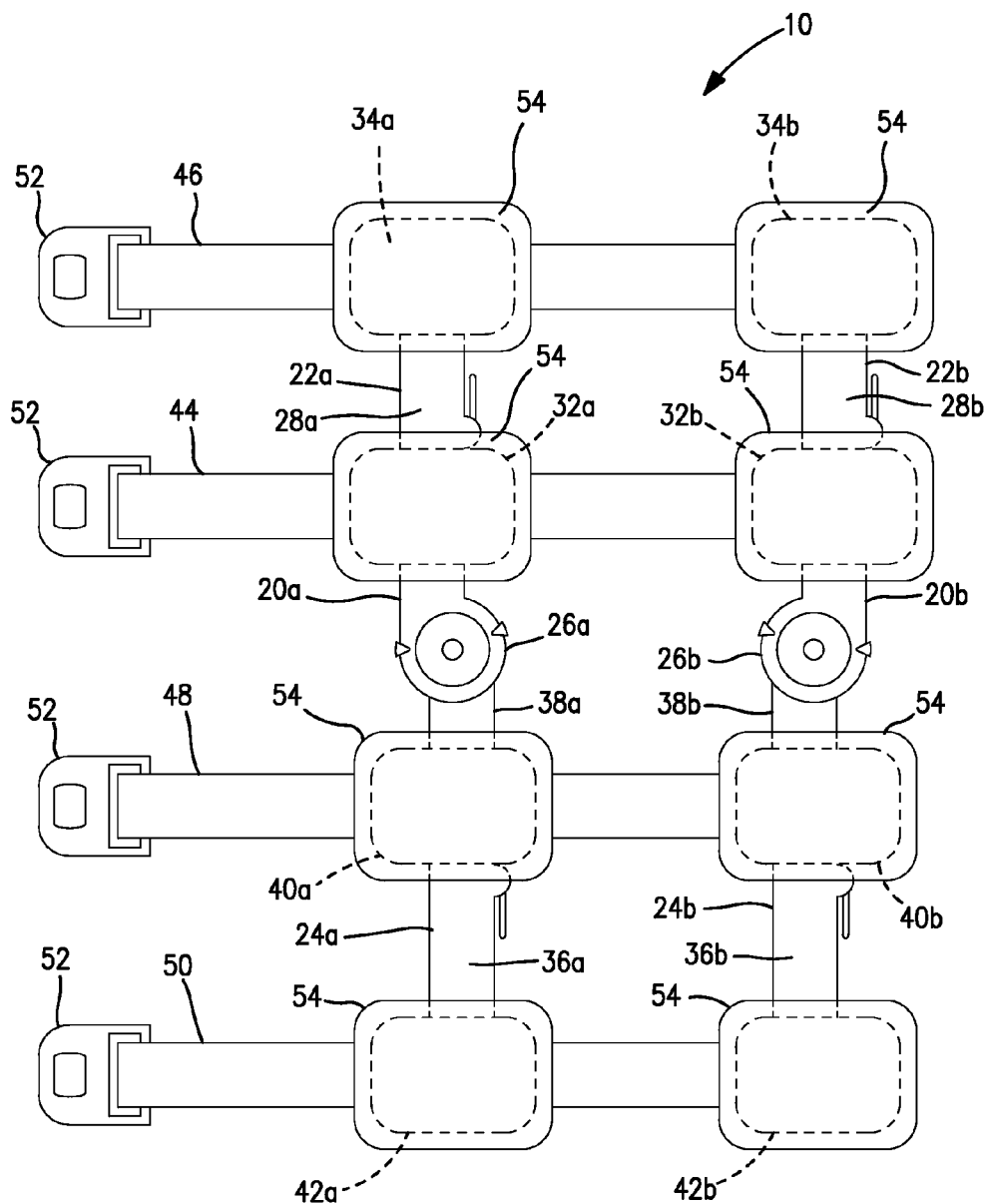
FIG. 2 is a plan view of the post-op knee brace of FIG. 1 laid out on a horizontal plane before mounting on the leg of a wearer.

Referring additionally to FIG. 2, the post-op knee brace 10 comprises a hinged frame and a plurality of securing straps. The hinged frame includes a hinged lateral frame assembly 20a configured to abut the lateral side of the leg 12 and a hinged medial frame assembly 20b configured to abut the medial side of the leg 12. When the post-op knee brace 10 is mounted on the fully-extended leg 12 of the patient wearer while standing as shown in FIG. 1, the lateral and medial frame assemblies 20a, 20b of the post-op brace 10 are substantially vertically oriented adjacent to the lateral and medial sides of the leg 12, respectively. The hinged lateral frame assembly 20a comprises a substantially rigid lateral upper support assembly 22a, a substantially rigid lateral lower support assembly 24a, and a lateral hinge assembly 26a. Both the lateral upper and lower support assemblies 22a, 24a are affixed to the lateral hinge assembly 26a and are rotatable about the lateral hinge assembly 26a with respect to one another.

The lateral upper support assembly 22a comprises a substantially rigid lateral upper housing 28a and a substantially rigid lateral upper support member 30a which can be telescoped within the lateral upper housing 28a to selectively adjust the length of the lateral upper support assembly 22a in accordance with the size and needs of the patient wearer of the post-op knee brace 10. The lateral upper support assembly 22a further comprises an arcuate and substantially rigid first lateral upper cuff 32a attached to the lateral upper support member 30a and an arcuate and substantially rigid second lateral upper cuff 34a attached to the lateral upper housing 28a. When the post-op knee brace 10 is mounted on the leg 12 of the patient wearer, the arcuate first and second lateral upper cuffs 32a, 34a engage the arcuate contours of the upper leg 16, thereby facilitating fitted mounting thereon.

The lateral lower support assembly 24a correspondingly comprises a lateral lower housing 36a, lateral lower support member 38a, first lateral lower cuff 40a and second lateral lower cuff 42a. The above-recited structural elements of the lateral lower support assembly 24a have analogous structural and functional characteristics as the corresponding structural elements of the lateral upper support assembly 22a recited above, but with respect to the lower leg 18.

The hinged lateral and medial frame assemblies 20a, 20b have substantially the same construction. As such, the structural elements of the hinged medial frame assembly 20b correspond to like elements of the hinged lateral frame assembly 20a and are identified by the same reference numbers, but with the suffix "b". In particular, the hinged medial frame assembly 20b comprises a medial upper support assembly 22b, a medial lower support assembly 24b, and a medial hinge assembly 26b. The medial upper support assembly 22b comprises a medial upper housing 28b, medial upper support member 30b, first medial upper cuff 32b and second medial upper cuff 34b. The medial lower support assembly 24b comprises a medial lower housing 36b, medial lower support member 38b, first medial lower cuff 40b and second medial lower cuff 42b.

The securing straps of the post-op knee brace 10 include first and second upper securing straps 44, 46 and first and second lower securing straps 48, 50. The first upper securing strap 44 is configured to wrap around the upper leg 16 while engaging the first lateral and medial upper cuffs 32a, 32b. The first lateral and medial upper cuffs 32a, 32b are provided with strap guides or retainers (not shown) which maintain the first upper securing strap 44 in engagement with the first lateral and medial upper cuffs 32a, 32b. The second upper securing strap 46 is also configured to wrap around the upper leg 16, but while engaging the second lateral and medial upper cuffs 34a, 34b, which are also provided with strap guides or retainers (not shown) to maintain the second upper securing strap 46 in engagement with the second lateral and medial upper cuffs 34a, 34b. The first lower securing strap 48 is configured to wrap around the lower leg 18 while engaging the first lateral and medial lower cuffs 40a, 40b which are provided with strap guides or retainers (not shown) to maintain the first lower securing strap 48 in engagement with the first lateral and medial lower cuffs 40a, 40b. The second lower securing strap 50 is also configured to wrap around the lower leg 18, but while engaging the second lateral and medial lower cuffs 42a, 42b, which are also provided with strap guides or retainers (not shown) to maintain the second lower securing strap 50 in engagement with the second lateral and medial lower cuffs 42a, 42b. An end of each of the securing straps 44, 46, 48, 50 is provided with a strap connection member 52 which enables releasable attachment of the end of the securing strap 44, 46, 48, 50 to a respective cooperative strap connection hook (not shown) provided on each of the medial upper and lower cuffs 32b, 34b, 40b, 42b, thereby facilitating mounting, removal and fitted remounting of the post-op knee brace 10 on the leg 12 of the patient wearer.

FIGS. 1 and 2 show the post-op knee brace 10 with conventional pads 54 having a unitary foam construction of the type described in U.S. Patent Application Publication Nos. 2006/0155229 A1 and 2006/0155232 A1. Each of the conventional pads 54 is configured in correspondence with the configuration of its respective cuff 32a, 32b, 34a, 34b, 40a, 40b, 42a and 42b and is releasably attached thereto. Releasable attachment may be effected by any known releasable attachment means. Preferred releasable attachment means are hook and loop fasteners available under the trademark VELCRO, wherein a patch 56, which is the hook material of the hook and loop fastener, is affixed to the inner surface 58 of each of the cuffs by substantially any permanent fastening means such as glue or the like. See FIG. 3 with respect to the first lateral lower cuff 40a. The outer surface of the conventional pads 54 includes a fabric (not shown) which is the loop material of the hook and loop fastener.

In accordance with one embodiment, practice of the present invention is performed by selectively detaching at least one of the conventional pads from its respective cuff on the post-op knee brace. A padding assembly of the present invention is then substituted for the detached conventional pad by releasably attaching the padding assembly to the respective cuff on the post-op knee brace from which the conventional pad has been detached. The padding assembly is selectively configured by a user to provide the padding assembly with a wound bridge either before or after attaching the padding assembly to the cuff. The term "user" as employed herein is intended to broadly encompass the patient wearer him/herself or health care professionals, care givers, or other like individuals tending to the patient wearer unless stated or implied otherwise by a given context herein. In any case, once the padding assembly is configured, the post-op knee brace is mounted on the leg of a patient wearer so that the padding assembly is positioned between the brace and the body of the wearer and the wound bridge on the padding assembly aligns with a surface wound on the leg of the patient wearer. The padding assembly contacts the skin of the wearer away from the surface wound, but the wound bridge maintains a sufficient clearance between the surface wound and padding assembly so that the padding assembly substantially avoids contact with the surface wound. As a result, the wound bridge advantageously exposes the surface wound to the surrounding air and substantially prevents the padding assembly from pressing against the surface wound, thereby taking pressure off of the surface wound.

A specific example of this practice is disclosed below with continuing reference to FIG. 3, wherein the conventional pad 54 is releasably detached from the first lateral lower cuff 40a and the detached conventional pad 54 is set aside from the post-op knee brace 10. Detachment is effected simply by manually pulling the conventional pad 54 away from the first lateral lower cuff 40a, thereby disengaging the loop material fixed to the outer surface (not shown) of the pad 54 from the patch 56 of hook material fixed to the inner surface 58 of the first lateral lower cuff 40a.

Figure 5:
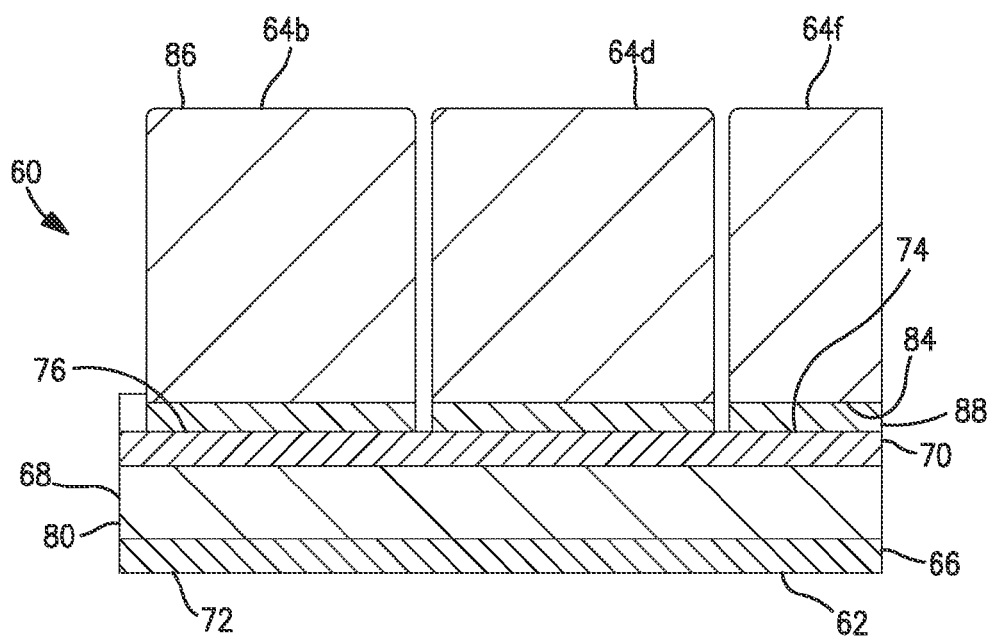
FIG. 5 is a partial sectional view of the padding assembly of FIG. 4 taken along line 5-5 in FIG. 4.

An embodiment of a padding assembly of the present invention which can be configured and substituted for the detached conventional pad 54 is shown in FIGS. 4 and 5 and generally designated 60. The padding assembly 60 comprises a base pad 62 and a plurality of bridging segments 64 which are selectively releasably attachable to the base pad 62 as well as being selectively releasably detachable from the base pad 62. The base pad 62 preferably has an integrated laminate construction comprising three layers in series, namely a first external layer 66, an internal layer 68 and a second external layer 70. The first and second external layers 66, 70 are continuously and permanently bonded to the internal layer 68 along substantially the entirety of the opposite faces of the internal layer 68, respectively, to create an essentially unitary structure. As such, the first external layer 66 forms the outer surface 72 of the base pad 62 and the second external layer 70 forms the inner surface 74 of the base pad 62. Bonding is effected by substantially any conventional bonding means such as gluing, thermal welding, ultrasonic welding, or the like.

The base pad 62 is characterized as non-rigid or relatively less rigid and more flexible than the rigid first lateral lower cuff 40a of the post-op knee brace 10. The flexibility of the base pad 62 is attributable to the relatively pliable, i.e., flexible, materials from which the base pad 62 is constructed. In particular, the first and second external layers 66, 70 are preferably constructed from a cloth material such as a plush or a pile which is capable of functioning as a loop material for a hook and loop fastener. The internal layer 68 is preferably constructed from an elastically compressible material, such as an open-cell or closed-cell foam or other sponge-like material.

Figure 6:
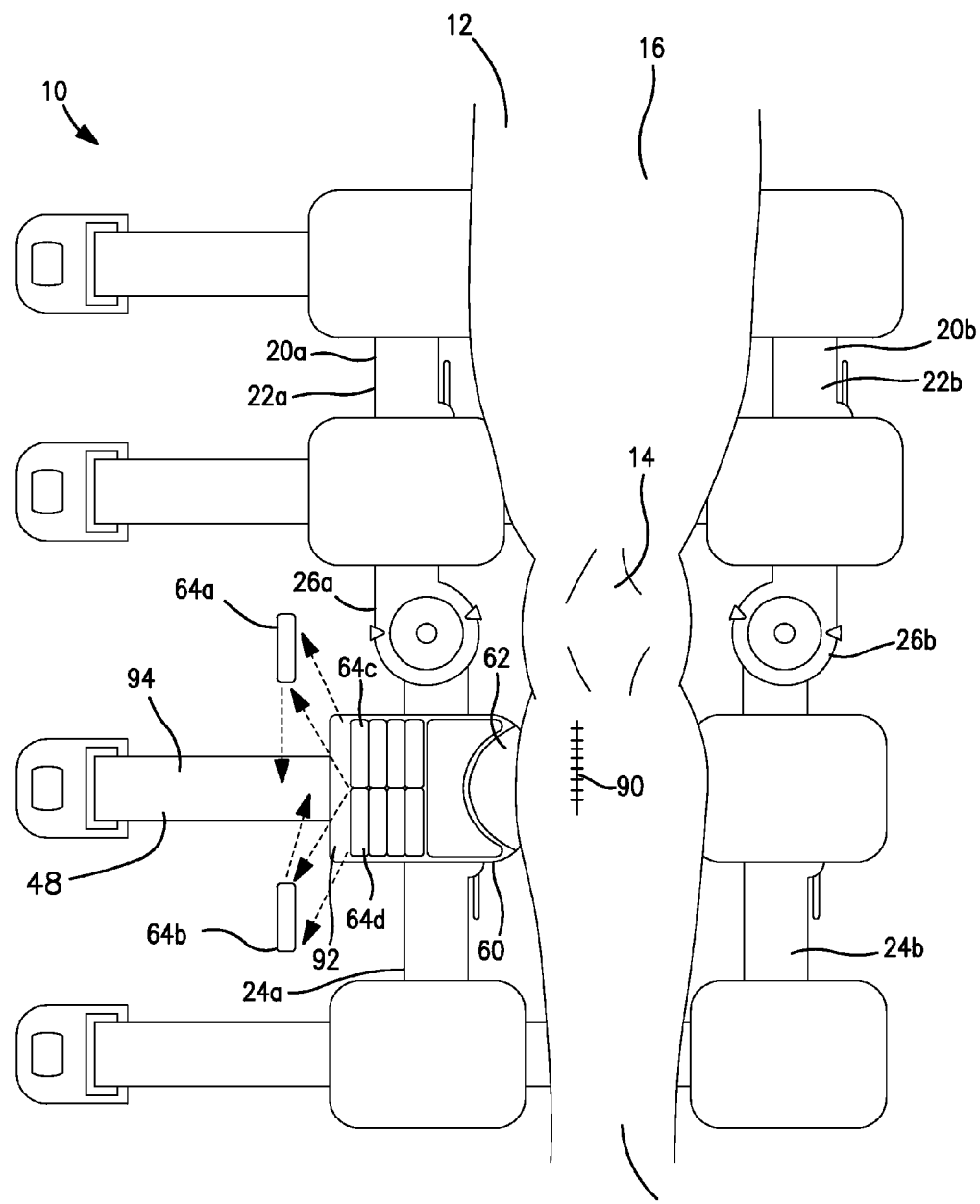
FIG. 6 is a plan view of the post-op knee brace of FIG. 3 with the padding assembly of FIG. 4 attached thereto, wherein the brace is being fitted to the leg of a wearer having a surface wound proximal to the knee and wherein the padding assembly is being configured to provide a wound bridge over the surface wound when the associated post-op knee brace is mounted on the leg of the wearer.

The outline of the base pad 62 is configured in correspondence with the outline of the first lateral lower cuff 40a. As such, the outer surface 72 of the base pad 62, which is preferably relatively even and smooth, covers the inner surface 58 of the first lateral lower cuff 40a, which is likewise relatively even and smooth, in substantially the same manner as the conventional pad 54. Since the base pad 62 is pliant, it can be flexed from its essentially planar construction into cooperative conforming engagement with the curved contours of the inner surface 58 of the first lateral lower cuff 40a. Substitution of the padding assembly 60 for the detached conventional pad 54 on the post-op brace 10 as shown in FIG. 6 is effected simply by manually placing the outer surface 72 of the base pad 62 against the inner surface 58 of the first lateral lower cuff 40a, thereby engaging the loop material fixed to the outer surface 72 of the base pad 62 with the patch 56 of hook material fixed to the inner surface 58 of the first lateral lower cuff 40a.

It is noted that hook and loop fasteners are recited throughout this disclosure as preferred means for achieving releasable attachment whenever called for. However, it is understood that the present invention is not limited thereby. Essentially any known alternate releasable attachment means can be substituted where appropriate for the hook and loop fasteners disclosed herein and falls within the scope of the present invention.

The inner surface 74 of the base pad 62 is characterized as being segmented into two adjoining areas 76, 78 which are distinguishable from one another by their different thicknesses. The first area 76 is an expansive, substantially smooth even area coextensive with a first end 80 of the inner surface 74 and defines a mounting substrate for the bridging segments 64. The second area 78 is a raised area coextensive with a second end 82 of the inner surface 74 opposite the first end 80 and defines a raised pad portion. The second area 78 is characterized as having a thickness and correspondingly a height greater than that of the first area 76 due to a thickening of the internal layer 68 of the base pad 62 where it underlies the second area 78.

All of the bridging segments 64 preferably have substantially the same construction as one another. Each bridging segment 64 is preferably characterized as having a first surface 84 and a second surface 86 on opposite faces thereof. Substantially the whole of each bridging segment 64 is preferably constructed from the same or similar material as the internal layer 68 of the base pad 62, i.e., an elastically compressible material such as an open-cell or closed-cell foam or other sponge-like material. However, a thin patch 88 of hook material is preferably permanently bonded to the elastically compressible material on the first surface 84 of each bridging segment 64.

Although commonly constructed, one or more of the bridging segments 64 may be differently shaped with respect to each other as shown in the present embodiment. The present plurality of bridging segments 64 includes bridging segments 64a, 64b, 64c, 64d, 64e, 64f, 64g, 64h, 64i, and 64j, all having the same raised uniform bar-like shape. The plurality of bridging segments 64 also includes the bridging segment 64k, having a more expansive, raised, irregular shape. It is alternatively within the scope of the present invention to configure all of the bridging segments of the padding assembly in the same shape.

Selective releasable attachment of the bridging segments 64 to the first area 76 on the inner surface 74 of the base pad 62 enables the user to arrange the bridging segments 64 in substantially any desired array on the first area 76. Selective releasable attachment of the bridging segments 64 to the first area 76 is preferably enabled by the patch 80 of hook material fixed to the first surface 82 of the bridging segment 64 and the loop material fixed to the inner surface 74 of the base pad 62.

In the present embodiment, the padding assembly 60 is initially supplied to the user with a full complement of bridging segments 64 releasably attached to the base pad 62. The bridging segments 64 form a continuous fully-populated array which covers substantially the entire first area 76 on the inner surface 74 of the base pad 62 as shown in FIGS. 4 and 5. The thickness and correspondingly the height of the padding assembly 60 across the first area 76 having the continuous array of bridging segments 64 (which is equal to the combined thickness of the bridging segments 64 and base pad 62 within that area) is preferably substantially the same as the thickness and height of the padding assembly 60 across the second area 78 of the base pad 62 (which is equal to the thickness of the base pad 62 alone within that area).

Referring to FIG. 6, the user reconfigures the continuous array of bridging segments 64 on the first area 76 of the base pad 62 in correspondence with a surface wound 90 on the lower leg 18 of the patient wearer after first determining what portion of the first area 76 will align with the surface wound 90 when the post-op brace 10 is properly positioned and mounted on the leg 12. In the present embodiment, it is determined that the portion of the first area 76 adjoining the first end 84 of the base pad 62 will align with the surface wound 90. Therefore, the continuous array of bridging segments 64 is reconfigured by selecting the bridging segments 64a, 64b, which populate this portion of the first area 76 adjacent to the first end 84 of the base pad 62, and detaching them from the first area 76.

Removing the bridging segments 64a, 64b effectively reconfigures the continuous array of bridging segments 64 on the first area 76 to a gapped partially-populated array of bridging segments 64 in accordance with the present invention. More particularly, removing the bridging segments 64a, 64b creates a vacant gap on the first area 76 at the first end 84 of the base pad 62 which was previously occupied by the detached bridging segments 64a, 64b and exposes the inner surface 74 of the base pad 62. The resulting gap 92 is termed a wound bridge and is characterized as having a thickness equal to the thickness of the base pad 62 alone in the first area 76. This thickness is substantially less than the thickness of the remainder of the padding assembly 60 which includes the second area 78 and the remainder of the first area 76 populated by the remaining bridging segments 64c, 64d, 64e, 64f, 64g, 64h, 64i, 64j and 64k.

Since the wound bridge 92 is positioned at the edge of the first end 84 of the base pad 62, it is apparent from FIG. 6 that only one side of the wound bridge 92 would be bounded by thickened padding when the post-op knee brace 10 is mounted on the leg 12 if no further steps are taken with respect to configuring the brace padding. Although the bridging segments 64c, 64d would bound the lateral side of the wound bridge 92, the opposite medial side of the wound bridge 92 would only be bounded by the overlying first lower securing strap 48 which would angle downwardly toward the surface wound 90 as the first lower securing strap 48 extended medially past the bridging segments 64c, 64d.

It has been found that the wound bridge 92 is most effective in maintaining the desired clearance between the padding assembly 60 and the surface wound 90 when the wound bridge 92 is bounded on both its lateral and medial sides by thickened padding rather than on just one of its sides. Therefore, the user preferably positions one or more additional wound bridging segments on the medial side of the wound bridge 92 by releasably attaching the additional wound bridging segment(s) to an additional supplemental mounting substrate medially adjacent to the wound bridge 92.

In accordance with a preferred embodiment, the one or more additional wound bridging segments are the bridging segments 64a, 64b which have been detached from the first area 76 of the base pad 62. The user serially attaches the detached bridging segments 64a, 64b to the inner surface 94 of the first lower securing strap 48 at adjacent locations on the inner surface 94 immediately medial to where the first lower securing strap 48 passes over the surface wound 90. Releasable attachment of the bridging segments 64a, 64b to the first lower securing strap 48 is enabled by constructing the inner surface 94 of the first lower securing strap 48 from a loop material. Accordingly, the inner surface 94 of the first lower securing strap 48 functions as an additional mounting substrate for bridging segments 64a, 64b, thereby supplementing the mounting substrate function of the first area 76 of the base pad 62. As a result of the above-described placement of the bridging segments 64c, 64d and 64a, 64b on the base pad 62 and first lower securing strap 48, respectively, the wound bridge 92 is advantageously laterally bounded by the bridging segments 64c, 64d and medially bounded by the bridging segments 64a, 64b to maintain the desired clearance between the padding assembly 60 and the surface wound 90.

In accordance with an alternate embodiment, the bridging segments 64a, 64b are set aside from the post-op knee brace 10 after detachment from the base pad 62 and one or more additional bridging segments (not shown), which are not included in the original continuous array of bridging segments 64, are separately provided in conjunction with the padding assembly 60 for use in reconfiguring the brace padding. Instead of reusing the detached bridging segments 64*a*, 64*b* which have been set aside, two separately-provided additional bridging segments are releasably attached to the inner surface 94 of the first lower securing strap 48 in substantially the same manner as described above with respect to the detached bridging segments 64*a*, 64*b*. As such, the additional bridging segments preferably have substantially the same construction and shape as the bridging segments 64*a*, 64*b*.

In yet another alternative, the user can obtain the additional bridging segments which are to be attached to the lower securing strap 48 in the manner of the above-described bridging segments 64*a*, 64*b* from among the original continuous array of bridging segments 64. In particular, redundant bridging segments from among the original continuous array of bridging segments 64 which are distally positioned away from the wound bridge 92, e.g., bridging segments 64*i*, 64*j* distally positioned away from the first end 84 of the base pad 62, can also be detached from the base pad 62 simultaneous with detachment of the bridging segments 64*a*, 64*b*. The bridging segments 64*i*, 64*j* are then releasably attached to the inner surface 94 of the first lower securing strap 48 in substantially the same manner as described above with respect to the detached bridging segments 64*a*, 64*b*.

Figure 7:
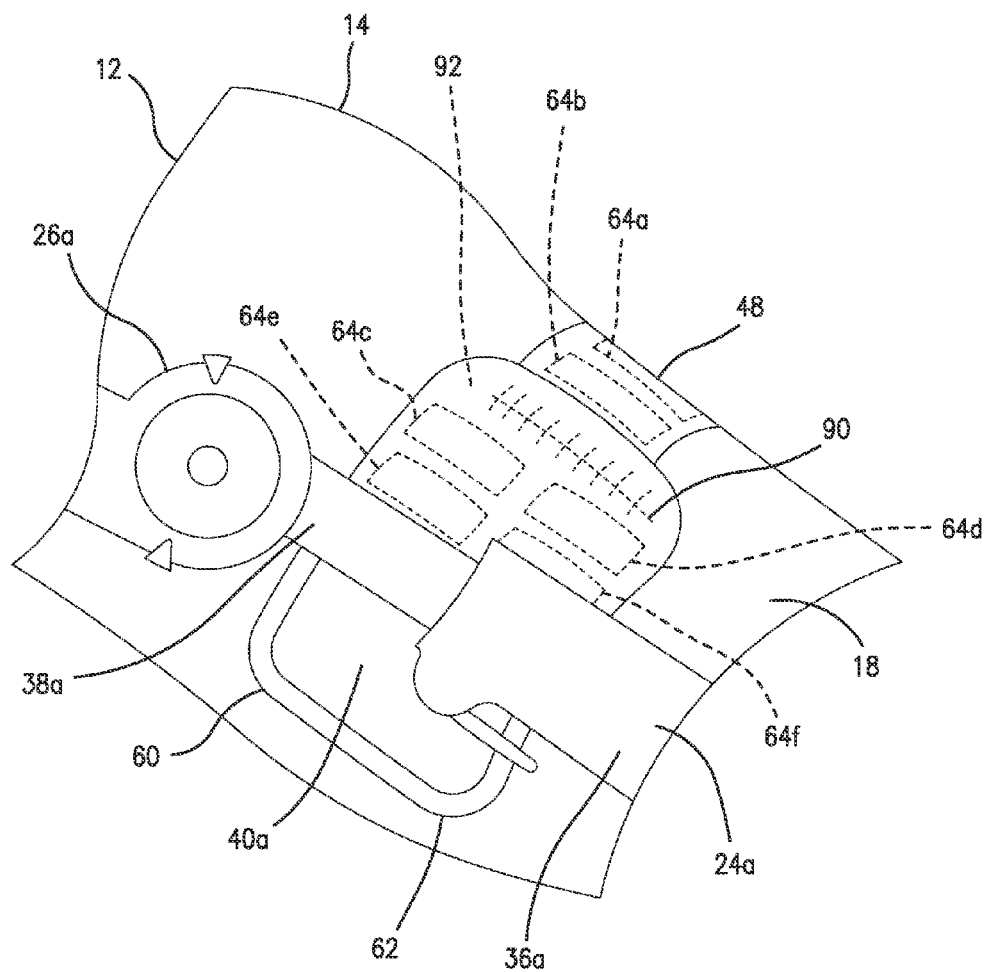
FIG. 7 is a perspective view of the post-op knee brace and attached padding assembly mounted on the leg of the wearer, wherein the padding assembly is configured to provide a wound bridge over the surface wound on the leg and wherein the adjacent cuff and securing strap are partially cutaway for clarity.

Although the above-recited padding assembly alignment and reconfiguration steps are shown in FIG. 6 as being performed while the padding assembly 60 is attached to the post-op knee brace 10, it is readily apparent that it is alternatively within the scope of the present invention to perform these steps while the padding assembly 60 is detached from the post-op knee brace 10. In any case, once the padding assembly 60 is reconfigured and releasably attached to the post-op knee brace 10, the brace 10 is in a condition for mounting on the leg 12 of the patient wearer. Referring to FIG. 7, the post-op knee brace 10 and attached padding assembly 60 are shown mounted on the leg 12 of the patient wearer. The padding assembly 60 is configured to provide an effective wound bridge 90 over the surface wound 92 on the leg 12.

An advantageous characteristic of the present padding assembly 60 is that the user can reconfigure the array of bridging segments 64 on the base pad 62 and/or adjacent securing straps 44, 46, 48, 50 as often as desired at any time throughout the life of the padding assembly 60 in accordance with the teaching herein. Multiple reconfiguring of the array of bridging segments 64 is enabled by the two-way releasable attachment and detachment character of the VELCRO couplings disclosed herein for attaching the bridging segments 64 to a mounting substrate or for detaching the bridging segments 64 from a mounting substrate. In this case, the mounting substrate is either the inner surface 58 of the first lateral lower cuff 40*a* or the inner surface 94 of the first lower securing strap 48.

The ability to reconfigure the array of bridging segments 64 multiple times advantageously permits the user to adapt the padding assembly 60 to changing conditions during the post-op recovery period. For example, the user may wish to adjust the length of the post-up knee brace 10 at some time during the recovery period which alters the relative positions of the padding assembly 62 on the brace 10 and the surface wound 92. In this case, the array of bridging segments 64 can be reconfigured to adapt to the new position of the padding assembly 60 relative to the surface wound 92 by reattaching the previously detached bridging segments 64 to their original positions on the pad base 62 (or attaching additional alternate bridging segments to these same positions) and detaching other bridging segments 64 such that the wound bridge 90 is shifted on the padding assembly 60 to align with the new position of the padding assembly 60 relative to the surface wound 92.

It is apparent from the above that the specific configuration of the gapped array of bridging segments described herein with reference to FIGS. 3-7 is but one example of a configuration of a gapped array of bridging segments within the scope of the present invention. The present invention further contemplates any number of alternate configurations for the bridging segments on the mounting substrate(s) of the orthopedic brace. Alternate configurations are achieved by selecting and detaching one or more alternate bridging segments from the base pad other than those disclosed above, thereby relocating the wound bridge on the padding assembly in correspondence with the alternately detached bridging segment(s) and likewise in correspondence with an alternate location of the surface wound relative to the position of the orthopedic brace when mounted on the patient wearer.

As a specific example, the bridging segments 64*c*, 64*d* could alternatively be detached from the first area 76 of the base pad 62 and set aside, rather than the bridging segments 64*a*, 64*b* as described above. Consequently, the wound bridge 92 would be relocated to a portion of the first area 76 more distal from the first end 80 of the base pad 62, which was previously occupied by the detached bridging segments 64*c*, 64*d*. The wound bridge 92 would be laterally bounded by the remaining bridging segments 64*e*, 64*f* and medially bounded by the remaining bridging segments 64*a*, 64*b* with both sets of bridging segments 64*a*, 64*b* and 64*e*, 64*f* utilizing the first area 76 on the inner surface 74 of the base pad 62 as the mounting substrate, thereby obviating the mounting substrate function of the first lower securing strap 48.

It is further apparent that the specific sizing and shaping of the first and second areas 76, 78 of the present base pad 62 as well as the sizing and shaping of the bridging segments 64 are specifically designed in correspondence with the specific configuration of the present post-op knee brace 10. In particular, it is apparent that the present design of the base pad 62 and bridging segments 64 contemplates that the surface wound 90 will typically be aligned with the first area 76 of the base pad 62 when the padding assembly 60 is releasably attached to a cuff 32*a*, 32*b*, 34*a*, 34*b*, 40*a*, 40*b*, 42*a* or 42*b* on the post-op knee brace 10 and the post-op knee brace 10 is in turn properly mounted on the leg 12. However, it is understood that it is within the scope of the present invention to modify the design of the padding assembly 60 for alternate attachment points on the post-op knee brace 10 and/or for alternate locations of the surface wound 90 on the leg 12. In particular, the design of the base pad 62 can be modified for correspondence with and attachment to alternate support members of the post-op knee brace 10 such as the hinge assemblies 26*a*, 26*b*, housings 28*a*, 28*b*, 36*a*, 36*b*, etc. The design of the base pad 62 and bridging segments 64 can also be modified for more universal applicability to alternate locations of the surface wound 92. This can be achieved, for example, by eliminating the raised pad portion 78 from the inner surface 74 of the base pad 62 altogether, extending the mounting substrate 76 across the entire inner surface 74 of the base pad 62, eliminating the expansive irregular bridging segment 64*k* and adding additional uniform bridging segments 64 shaped in the manner of the bridging segment 64*a*.

The above description applies to cases where the padding assemblies of the present invention are configured in correspondence with a particular embodiment of an associated orthopedic brace (i.e., post-op knee brace) for a particular body part (i.e., knee joint) and for a particular surface wound location (i.e., lower lateral side of the knee joint). However, it is readily apparent to one of ordinary skill in the art that the instant teaching for configuring padding assemblies in correspondence with the specific orthopedic brace, body part and surface wound location disclosed herein can be applied generally to configure padding assemblies in correspondence with substantially any alternate orthopedic brace, either rigid, soft or combination thereof, as well as in correspondence with any number of alternate body parts and surface wound locations and such alternate configurations of the padding assembly fall within the scope of the present invention. It is further apparent to one of ordinary skill in the art that the instant teaching for configuring padding assemblies in correspondence with particular support members of the orthopedic brace specifically disclosed herein can be applied to configure padding assemblies in correspondence with other support members of the orthopedic brace specifically disclosed herein and such alternate configurations of the padding assembly fall within the scope of the present invention.

Figure 9:
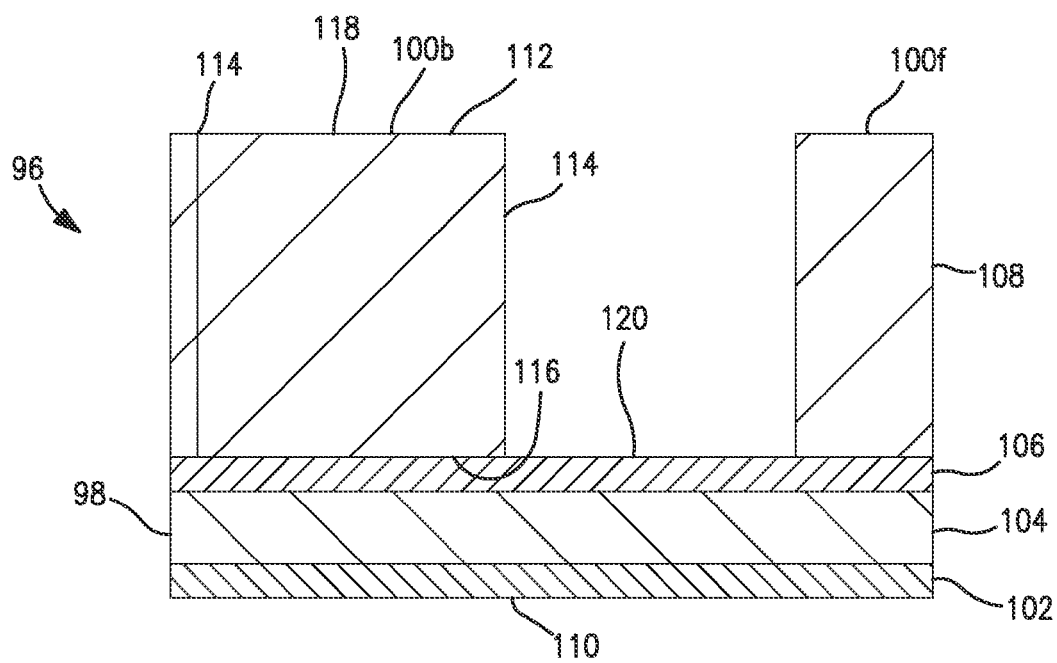
FIG. 9 is a partial sectional view of the alternate padding assembly of FIG. 8 taken along line 9-9 in FIG. 8.

Referring to FIGS. 8 and 9, an alternate embodiment of a padding assembly of the present invention is shown and generally designated 96. The padding assembly 96 can be configured and substituted for a conventional pad on an associated orthopedic brace, such as the post-op knee brace 10 of FIG. 1, in substantially the same manner as described above with respect to the padding assembly 60. Like the padding assembly 60, the present padding assembly 96 comprises a base pad 98 and a continuous array of bridging segments 100 releasably attached to the base pad 98 which can be reconfigured to form a gapped array of the bridging segments 100. However, a substantial difference between the construction of the padding assembly 60 and the construction of the padding assembly 96 is the means by which the bridging segments 100 are releasably attached to the base pad 98 of the padding assembly 96.

The padding assembly 96 preferably has an integrated laminate construction comprising four layers in series. The first three layers are a first external layer 102, a first internal layer 104 and a second internal layer 106 which in combination comprise the base pad 98. The remaining layer is a second external layer 108 which comprises a continuous array of bridging segments 100. One face of the first external layer 102 is continuously and permanently bonded to a face of the first internal layer 104, the remaining opposite face of the first internal layer 104 is continuously and permanently bonded to a face of the second internal layer 106, and the remaining opposite face of the second internal layer 106 which forms the inner surface of the base pad 98 is continuously and permanently bonded to a face of the second external layer 108 to create an essentially unitary structure. A permanent bond as the term is used herein means that the two bonded materials cannot be separated without physically destroying the bond, i.e., in the present case, forcibly tearing the material of the second internal layer 106 in a manner described. In any case, the unbonded open face of the first external layer 102 forms the outer surface 110 of the padding assembly 96 and correspondingly the base pad 98. The unbonded open face of the second external layer 108 forms the inner surface 112 of the padding assembly 96 which is characterized as a single expansive, substantially smooth even area.

Each layer of the padding assembly 96 is constructed from relatively pliable flexible materials. In particular, the first external layer 102 is preferably constructed from a cloth material which is capable of functioning as a loop material for a hook and loop fastener. The remaining layers 104, 106, 108 are preferably constructed from elastically compressible materials. The first internal layer 104 and second external layer 108 may be constructed from the same or different material, but regardless the material(s) of both layers 104, 108 is characterized as being relatively a high integrity material and resistant to tearing. In contrast the material of the second internal layer 106 is characterized as being a relatively low integrity material and conducive to tearing The continuous array of bridging segments 100 releasably attached to the base pad 98 is constructed by performing a series of cuts 114 in the inner surface 112 of the padding assembly 96 which extend through substantially the entire thickness of the second external layer 108 down to, but not through, the second internal layer 106. The pattern of the cuts 114 in the inner surface 112 corresponds to the desired outline of the individual bridging segments 100a, 100b, 100c, 100d, 100e, 100f, 100g, 100h, 100i. 100j, 100k, 100l, 100m, 100n, 100o, 100p, 100q, 100r making up the continuous array of bridging segments 100.

All of the bridging segments 100 preferably have substantially the same construction and uniform shape. In particular, each bridging segment 100 is preferably characterized as having a first surface 116 and a second surface 118 on opposite faces thereof. It is apparent that mounting the bridging segments 100 on the base pad 98 is effected by bonding the second internal layer 106 of the padding assembly 96 to the second external layer 108 as described above such that the second internal layer 106 on the base pad 98 functions as the mounting substrate for the bridging segments 100 which have first surfaces 116 bonded to the second internal layer 106.

Selective releasable detachment of the bridging segments 100 from the base pad 98 enables the user to create a gapped array of bridging segments 100 in substantially any desired configuration. Selective releasable detachment of the bridging segments 100 from the base pad 98 is enabled by the weak tear-away character of the second internal layer 106 which releasably attaches the bridging segment 100 and to the padding assembly 96. The second internal layer 106 enables the user to readily remove a selected bridging segment 100 from the continuous array of bridging segments 100 simply by manually gripping the second surface 118 of the selected bridging segment 100 and pulling the bridging segment 100 away from the base pad 98 with a sufficient force to tear the permanent bond between the second internal and external layers 106 and 108 at the first surface 116 of the selected bridging segment 100, thereby exposing the second internal layer 106 and/or first internal layer 104. A specific example of configuring the padding assembly 96 for use in association with the post-op knee brace 10 of FIG. 1 is described below.

Figure 3:
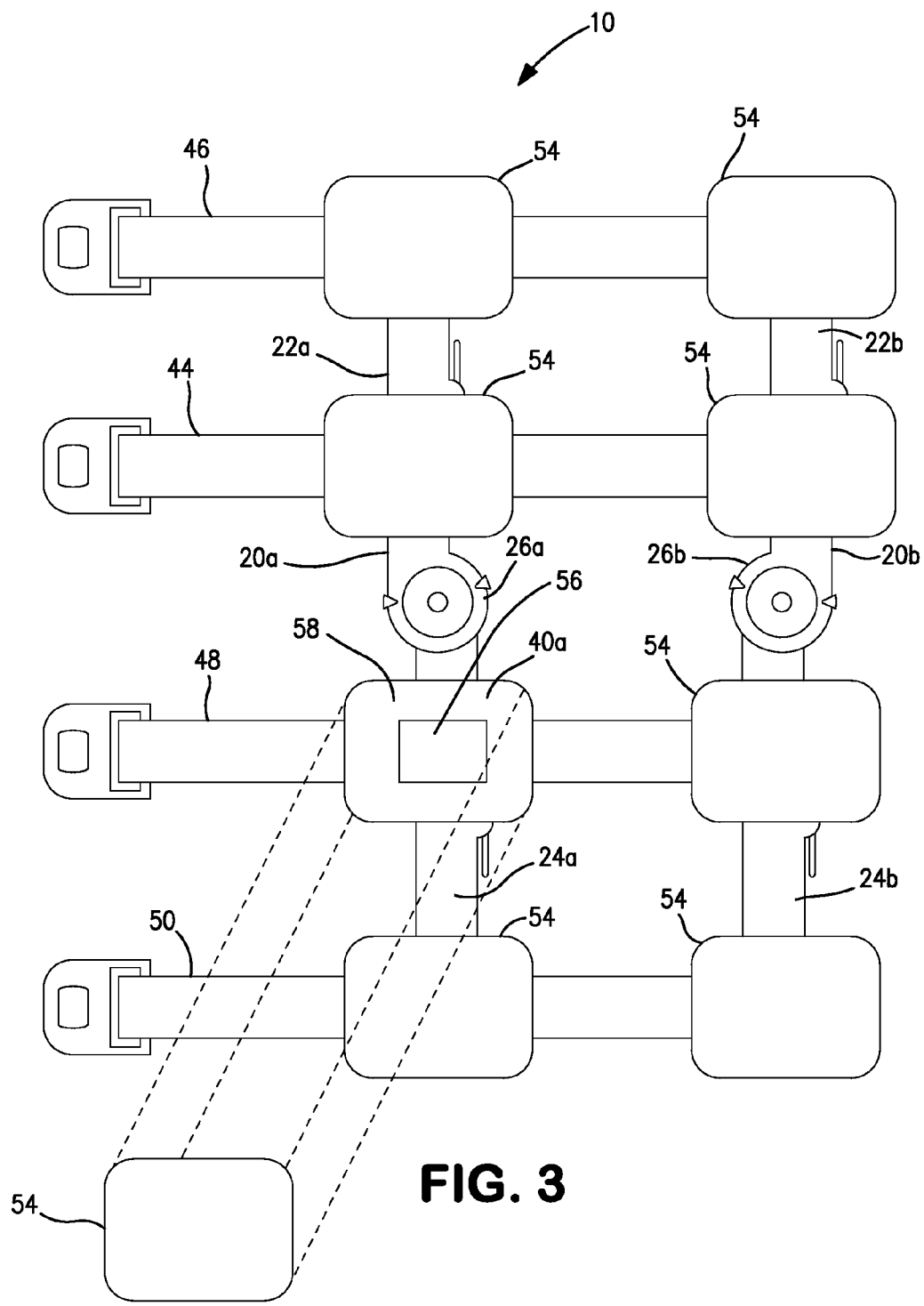
FIG. 3 is a plan view of the post-op knee brace of FIG. 1 in a modified condition, wherein a conventional pad has been detached from the brace in preparation for attachment of a padding assembly of the present invention to the brace in place of the conventional pad.

In accordance with the present embodiment, the outline of the padding assembly 96 is configured in correspondence with the outline of the first lateral lower cuff 40a and attached to the inner surface 58 of the first lateral lower cuff 40a by engaging the loop material of the first external layer 102 on the outer surface 110 of the padding assembly 96 with the patch 56 of hook material fixed to the inner surface 58 of the first lateral lower cuff 40a in FIG. 3. The user reconfigures the continuous array of bridging segments 100 in correspondence with a surface wound on the patient wearer (such as shown in FIG. 6) after determining that the portion of the inner surface 112 of the padding assembly 96 covered by the bridging segments 100c, 100d will align with a surface wound when the post-op brace 10 is properly positioned and mounted on the leg 12. In particular, the continuous array of bridging segments 100 is reconfigured by releasably, but permanently, detaching the bridging segments 100c, 100d from the padding assembly 96 in the manner described above and setting them aside.

Removing the bridging segments 100c, 100d effectively reconfigures the continuous array of bridging segments 100 to a desired gapped partially-populated array of bridging segments 100, thereby creating a wound bridge 120 on the base pad 98 previously occupied by the detached bridging segments 100c, 100d and exposing the second internal layer 106 and/or first internal layer 104. The resulting wound bridge 120 is laterally bounded by the remaining bridging segments 100a, 100b and medially bounded by the remaining bridging segments 100e, 100f. The wound bridge 120 is characterized as having a thickness equal to the thickness of the base pad 98 alone which is substantially less than the thickness of the remainder of the padding assembly 96 which includes the area populated by the remaining bridging segments 100a, 100b, 100e, 100f, etc.

It is apparent from the above that, unlike the padding assembly 60, selective releasable detachment of the bridging segments 100c, 100d from the continuous array of bridging segments 100 on the padding assembly 96 is permanent. Thus, once detached, the present embodiment does not provide any means for selectively releasably reattaching the bridging segments 100c, 100d to the base pad 98 or any other mounting substrate on the post-op knee brace 10. Accordingly, once the user has configured the padding assembly 96 a first time to a particular gapped array of bridging segments 100, the user cannot subsequently reconfigure the gapped array of bridging segments 100 by reattaching the previously detached bridging segments 100 to the base pad 98.

Although the above-recited padding assembly alignment and reconfiguration steps are described as being performed while the padding assembly 96 is attached to the post-op knee brace 10, it is readily apparent that it is alternatively within the scope of the present invention to perform these steps while the padding assembly 96 is detached from the post-op knee brace 10. In any case, once the padding assembly 96 is reconfigured and releasably attached to the post-op knee brace 10, the brace 10 is in a condition for mounting on the leg 12 of the patient wearer in substantially the same manner as shown with respect to the padding assembly 60.

While the forgoing preferred embodiments of the invention have been described and shown, it is understood that alternatives and modifications, such as those suggested and others, may be made thereto and fall within the scope of the invention.

I claim:

1. A padding assembly comprising:
a first surface of said padding assembly attachable to an associated orthopedic brace;
a second surface of said padding assembly;
a mounting substrate;
a first bridging segment releasably attached to said mounting substrate; and
a second bridging segment releasably attached to said mounting substrate, said first and second bridging segments included in a first array selectively reconfigurable to a second array by detaching said second bridging segment from said mounting substrate, thereby defining a first wound bridge area on said second surface of said padding assembly where said second bridging segment is detached and defining a first raised area on said second surface of said padding assembly where said first bridging segment is attached, wherein a thickness of said padding assembly at said first raised area is substantially greater than a thickness of said padding assembly at said first wound bridge area, and wherein a height of said second surface of said padding assembly at said first raised area is substantially greater than a height of said second surface of said padding assembly at said first wound bridge area.

2. The padding assembly of claim 1, wherein said first bridging segment is releasably attached to a first location on said mounting substrate in said first array and said second bridging segment is releasably attached to a second location on said mounting substrate in said first array, wherein said first wound bridge area is at said second location on said mounting substrate in said second array, wherein said first wound bridge area has a first side and a second side and is bounded on said first side by said first bridging segment and is bounded on said second side by an additional bridging segment, wherein said additional bridging segment defines a second raised area on said second surface of said padding assembly separated from said first raised area by said first wound bridge area, wherein a thickness of said padding assembly at said second raised area is substantially greater than the thickness of said padding assembly at said first wound bridge area, and wherein a height of said second surface of said padding assembly at said second raised area is substantially greater than the height of said second surface of said padding assembly at said first wound bridge area so that when an associated orthopedic brace is mounted on a body of a wearer with said padding assembly attached thereto, said first and second raised areas of said a padding assembly contact a body of a wearer while a thickness differential between said first and second raised areas and said first wound bridge area enables said first wound bridge area to avoid contacting a body of a wearer.

3. The padding assembly of claim 2, wherein said additional bridging segment is a third bridging segment not included in said first array and selectively releasably attached to said mounting substrate or selectively releasably attached to an alternate mounting substrate on said associated orthopedic brace, thereby bounding said second side of said first wound bridge area.

4. The padding assembly of claim 2, wherein said additional bridging segment is a third bridging segment releasably attached to a third location on said mounting substrate in said first array and releasably detached from said third location and selectively releasably re-attached to an alternate location on said mounting substrate or selectively releasably attached to an alternate mounting substrate on said associated orthopedic brace, thereby bounding said second side of said first wound bridge area.

5. The padding assembly of claim 2, wherein said first bridging segment, said second bridging segment and said additional bridging segment are elastically compressible.

6. The padding assembly of claim 2, wherein said first surface of said padding assembly is attachable to a rigid contoured surface of an associated orthopedic brace, said padding assembly further comprising a layer of pliable material extending between said first surface and said mounting substrate sufficiently pliant to enable cooperative conformance of said first surface and said mounting substrate with a rigid contoured surface of an associated orthopedic brace when said first surface of said padding assembly is attached thereto.

7. The padding assembly of claim 2, wherein said additional bridging segment is said second bridging segment releasably detached from said second location on said mounting substrate and selectively releasably re-attached to an alternate location on said mounting substrate or selectively releasably attached to an alternate mounting substrate on an associated orthopedic brace, thereby bounding said second side of said first wound bridge area.

8. The padding assembly of claim 7, wherein said alternate mounting substrate is a securing strap of an associated orthopedic brace.

9. A padding assembly comprising:
a first surface of said padding assembly attachable to an associated orthopedic brace;
a second surface of said padding assembly;
a mounting substrate;
a first bridging segment releasably attached to said mounting substrate; and
a second bridging segment releasably attached to said mounting substrate, said first and second bridging segments included in a first array selectively reconfigurable to a second array by detaching said second bridging segment from said mounting substrate, thereby defining a first wound bridge area on said second surface of said padding assembly where said second bridging segment is detached and defining a first raised area on said second surface of said padding assembly where said first bridging segment is attached, wherein a thickness of said padding assembly at said first raised area is substantially greater than a thickness of said padding assembly at said first wound bridge area, and wherein said second array is selectively reconfigurable to a third array by reattaching said detached second bridging segment to said mounting substrate at said first wound bridge area, thereby converting said first wound bridge area to a second raised area, and detaching said first bridging segment from said mounting substrate at said first raised area, thereby converting said first raised area to a second wound bridge area, wherein a thickness of said padding assembly at said second raised area is substantially greater than a thickness of said padding assembly at said second wound bridge area.

10. The padding assembly of claim 9, wherein said detached second bridging segment is selectively attachable to an alternate mounting substrate on an orthopedic brace.

11. The padding assembly of claim 10, wherein said alternate mounting substrate is a securing strap of an orthopedic brace.

12. The padding assembly of claim 9, further comprising a third bridging segment selectively attachable to an alternate mounting substrate on an orthopedic brace.

13. The padding assembly of claim 12, wherein said alternate mounting substrate is a securing strap of an orthopedic brace.

14. The padding assembly of claim 9, wherein said first surface of said padding assembly is attachable to a substantially rigid support member of an orthopedic brace.

15. A padding assembly comprising:
a first surface of said padding assembly attachable to an associated orthopedic brace;
a second surface of said padding assembly;
a mounting substrate;
a first bridging segment releasably attached to said mounting substrate; and
a second bridging segment releasably attached to said mounting substrate, said first and second bridging segments included in a first array selectively reconfigurable to a second array by detaching said second bridging segment from said mounting substrate, thereby defining a first wound bridge area on said second surface of said padding assembly where said second bridging segment is detached and defining a first raised area on said second surface of said padding assembly where said first bridging segment is attached, wherein a thickness of said padding assembly at said first raised area is substantially greater than a thickness of said padding assembly at said first wound bridge area, and wherein said second surface is on a substantially opposite side of said padding assembly from said first surface.

16. The padding assembly of claim 15, wherein said first bridging segment is releasably attached to a first location on said mounting substrate in said first array and said second bridging segment is releasably attached to a second location on said mounting substrate in said first array, wherein said first wound bridge area is at said second location on said mounting substrate in said second array, wherein said first wound bridge area has a first side and a second side and is bounded on said first side by said first bridging segment and is bounded on said second side by an additional bridging segment, wherein said additional bridging segment defines a second raised area on said second surface of said padding assembly separated from said first raised area by said first wound bridge area, wherein a thickness of said padding assembly at said second raised area is substantially greater than the thickness of said padding assembly at said first wound bridge area, and wherein a height of said second surface of said padding assembly at said second raised area is substantially greater than a height of said second surface of said padding assembly at said first wound bridge area so that when an associated orthopedic brace is mounted on a body of a wearer with said padding assembly attached thereto, said first and second raised areas of said a padding assembly contact a body of a wearer while a thickness differential between said first and second raised areas and said first wound bridge area enables said first wound bridge area to avoid contacting a body of a wearer.

17. The padding assembly of claim 16, wherein said additional bridging segment is said second bridging segment releasably detached from said second location on said mounting substrate and selectively releasably re-attached to an alternate location on said mounting substrate or selectively releasably attached to an alternate mounting substrate on an associated orthopedic brace, thereby bounding said second side of said first wound bridge area.

18. The padding assembly of claim 16, wherein said additional bridging segment is a third bridging segment not included in said first array and selectively releasably attached to said mounting substrate or selectively releasably attached to an alternate mounting substrate on said associated orthopedic brace, thereby bounding said second side of said first wound bridge area.

19. The padding assembly of claim 16, wherein said additional bridging segment is a third bridging segment releasably attached to a third location on said mounting substrate in said first array and releasably detached from said third location and selectively releasably re-attached to an alternate location on said mounting substrate or selectively releasably attached to an alternate mounting substrate on said associated orthopedic brace, thereby bounding said second side of said first wound bridge area.

20. The padding assembly of claim 16, wherein said first surface of said padding assembly is attachable to a rigid contoured surface of an associated orthopedic brace, said padding assembly further comprising a layer of pliable material extending between said first surface and said mounting substrate sufficiently pliant to enable cooperative conformance of said first surface and said mounting substrate with a rigid contoured surface of an associated orthopedic brace when said first surface of said padding assembly is attached thereto.

21. A padding assembly comprising:
- a base pad having a first surface and a second surface, wherein said first surface is attachable to an associated orthopedic brace;
- a first bridging segment releasably attached to a first location on a first mounting substrate on said second surface of said base pad; and
- a second bridging segment releasably attached to a second location, wherein a first wound bridge area is positioned on said first mounting substrate between said first bridging segment and said second bridging segment, and wherein a thickness of said padding assembly where said first bridging segment is attached to said first mounting substrate is substantially greater than a thickness of said padding assembly at said first wound bridge area, and further wherein a thickness of said second bridging segment is substantially greater than the thickness of said padding assembly at said first wound bridge area, wherein said first and second locations are on said first mounting substrate and said first and second bridging assemblies and said first wound bridge area are included in a first array; and
- a third bridging segment releasably attached to said first mounting substrate and included in said first array, wherein said first bridging segment is positioned between said third bridging segment and said second bridging segment and wherein a thickness of said padding assembly where said third bridging segment is attached to said first mounting substrate is substantially greater than the thickness of said padding assembly at said first wound bridge area, and wherein said first array is selectively reconfigurable to a second array by detaching said first bridging segment from said mounting substrate and attaching said first bridging segment or a fourth bridging segment of said padding assembly to said mounting substrate at said first wound bridge area, thereby converting said first wound bridge area to a raised area and defining a second wound bridge area where said first bridging segment is detached from said mounting substrate, and wherein a thickness of said padding assembly at said raised area is substantially greater than a thickness of said padding assembly at said second wound bridge area and a thickness of said padding assembly where said second bridging segment is attached to said first mounting substrate is substantially greater than the thickness of said padding assembly at said second wound bridge area.

22. The padding assembly of claim 21, wherein said second location is on said first mounting substrate on said second surface of said base pad.

23. The padding assembly of claim 21, wherein said second location is on a second mounting substrate on a securing strap or a support element of an orthopedic brace.

24. A padding assembly comprising:
- a base pad having a first surface and a second surface, wherein said first surface is attachable to an associated orthopedic brace;
- a first bridging segment releasably attached to a first mounting substrate on said second surface of said base pad; and
- a second bridging segment releasably attached to a second mounting substrate, wherein a first wound bridge area is positioned on said first mounting substrate between said first bridging segment and said second bridging segment, wherein a thickness of said padding assembly where said first bridging segment is attached to said first mounting substrate is substantially greater than a thickness of said padding assembly at said first wound bridge area, wherein a thickness of said second bridging segment is substantially greater than the thickness of said padding assembly at said first wound bridge area, wherein said first and second bridging segments and said first wound bridge are included in a first array selectively reconfigurable to a second array by detaching said second bridging segment from said second mounting substrate and attaching said second bridging segment or a third bridging segment of said padding assembly to said first mounting substrate at said first wound bridge area, thereby converting said first wound bridge area to a raised area and defining a second wound bridge area where said first bridging segment is detached from said mounting substrate, and wherein a thickness of said padding assembly at said raised area is substantially greater than a thickness of said padding assembly at said second wound bridge area and a thickness of said padding assembly where said second bridging segment is attached to said first mounting substrate is substantially greater than the thickness of said padding assembly at said second wound bridge area.

25. The padding assembly of claim 24, wherein said second mounting substrate is on a securing strap or a support element of an orthopedic brace.

26. A padding assembly comprising:
- a first surface of said padding assembly attachable to an associated orthopedic brace;
- a second surface of said padding assembly;
- a mounting substrate;
- a first bridging segment releasably attached to said mounting substrate;
- a second bridging segment releasably attached to said mounting substrate, said first and second bridging segments included in a first array selectively reconfigurable to a second array by detaching said second bridging segment from said mounting substrate, thereby defining a first wound bridge area on said second surface of said padding assembly where said second bridging segment is detached and defining a first raised area on said second surface of said padding assembly where said first bridging segment is attached, wherein a thickness of said padding assembly at said first raised area is substantially greater than a thickness of said padding assembly at said first wound bridge area; and
- a third bridging segment included in said first array and releasably attached to said mounting substrate, wherein said second bridging segment is positioned between said first and third bridging segments, wherein said second array defines a second raised area on said second surface of said padding assembly where said third bridging segment is attached, and wherein a thickness of said padding assembly at said second raised area is substantially greater than the thickness of said padding assembly at said first wound bridge area.

27. A padding assembly comprising:
- a first surface of said padding assembly attachable to an associated orthopedic brace;
- a second surface of said padding assembly;
- a mounting substrate;
- a first bridging segment releasably attached to said mounting substrate; and
- a second bridging segment releasably attached to said mounting substrate, said first and second bridging segments included in a first array selectively reconfigurable to a second array by detaching said second bridging segment from said mounting substrate, thereby defining a first wound bridge area on said second surface of said padding assembly where said second bridging segment is detached and defining a first raised area on said second surface of said padding assembly where said first bridging segment is attached, wherein a thickness of said padding assembly at said first raised area is substantially greater than a thickness of said padding assembly at said first wound bridge area, wherein a height of said second surface of said padding assembly at said first raised area is substantially greater than a height of said second surface of said padding assembly at said first wound bridge area, wherein said second array is selectively reconfigurable to a third array by reattaching said detached second bridging segment to said mounting substrate at said first wound bridge area, thereby converting said first wound bridge area to a second raised area, and detaching said first bridging segment from said mounting substrate at said first raised area, thereby converting said first raised area to a second wound bridge area, wherein a thickness of said padding assembly at said second raised area is substantially greater than a thickness of said padding assembly at said second wound bridge area, and wherein a height of said second surface of said padding assembly at said second raised area is substantially greater than a height of said second surface of said padding assembly at said second wound bridge area.

28. A padding assembly comprising:
a base pad having a first surface and a second surface, wherein said first surface is attachable to an associated orthopedic brace;
a first bridging segment releasably attached to a first mounting substrate on said second surface of said base pad; and
a second bridging segment releasably attached to said first mounting substrate, wherein a first wound bridge area is positioned on said first mounting substrate between said first bridging segment and said second bridging segment, wherein a thickness of said padding assembly where said first bridging segment is attached to said first mounting substrate is substantially greater than a thickness of said padding assembly at said first wound bridge area, wherein a thickness of said padding assembly where said second bridging segment is attached to said first mounting substrate is substantially greater than the thickness of said padding assembly at said first wound bridge area, wherein said first and second bridging segments and said first wound bridge are included in a first array selectively reconfigurable to a second array by detaching said first bridging segment from said mounting substrate and attaching said first bridging segment or a third bridging segment of said padding assembly to said mounting substrate at said first wound bridge area, thereby converting said first wound bridge area to a raised area and defining a second wound bridge area where said first bridging segment is detached from said mounting substrate, and wherein a thickness of said padding assembly at said raised area is substantially greater than a thickness of said padding assembly at said second wound bridge area and the thickness of said padding assembly where said second bridging segment is attached to said first mounting substrate is substantially greater than the thickness of said padding assembly at said second wound bridge area.

* * * * *